United States Patent [19]

Huybrechts, Robert

[11] Patent Number: 5,431,563
[45] Date of Patent: Jul. 11, 1995

[54] MOULDABLE COMPOSITION AND METHOD OF MAKING IT

[76] Inventor: Huybrechts, Robert, 18485 Keel Street North R.R. #2, New Market, Ontario, Canada, L3Y 4V9

[21] Appl. No.: 271,993

[22] Filed: Jul. 8, 1994

Related U.S. Application Data

[63] Continuation-in-part of Ser. No. 992,752, Dec. 18, 1992, abandoned.

[51] Int. Cl.$^6$ .................. A61C 11/00; C08F 265/06
[52] U.S. Cl. ........................ 433/48; 433/168.1; 433/199.1; 433/171; 433/214; 128/862; 523/109
[58] Field of Search .............. 433/48, 168.1, 199.1, 433/171, 214; 128/862; 523/109

[56] References Cited

U.S. PATENT DOCUMENTS

| | | |
|---|---|---|
| 4,161,065 | 7/1979 | Gigante .................................. 32/2 |
| 4,247,287 | 1/1981 | Gigante . |
| 4,248,807 | 2/1981 | Gigante . |
| 4,568,280 | 2/1986 | Ahlin ...................................... 433/6 |
| 4,759,798 | 7/1988 | von Nostitz ........................ 106/35 |
| 4,791,184 | 12/1988 | Nagai et al. ........................ 525/305 |
| 4,946,901 | 8/1990 | Lechner et al. .................... 525/305 |
| 5,051,482 | 9/1991 | Tepir ................................... 525/309 |
| 5,055,529 | 10/1991 | Kishida et al. ..................... 525/309 |
| 5,182,332 | 1/1993 | Yamamoto et al. ................ 525/305 |

*Primary Examiner*—Vasus S. Jagannathan

[57] ABSTRACT

A thermoplastic article formed of a composition for customizable molding parts of devices such as dental plates or hand grips or sports equipment comprises a composition which is set below 37° C. and is conformably moldable between about 50° C. and 95° C. The article can be molded, used, and re-molded and re-used, repeatedly. Such a composition may be an acrylate polymer, possibly a methacrylate polymer. The acrylate polymer may soften or become liquid in the range of 50° C. to 95° C. and may be mixed with another such polymer which is set at that temperature range so that a pasty moldable mass is formed, for example by warming in warm water. The invention includes a method of forming the composition.

4 Claims, 4 Drawing Sheets

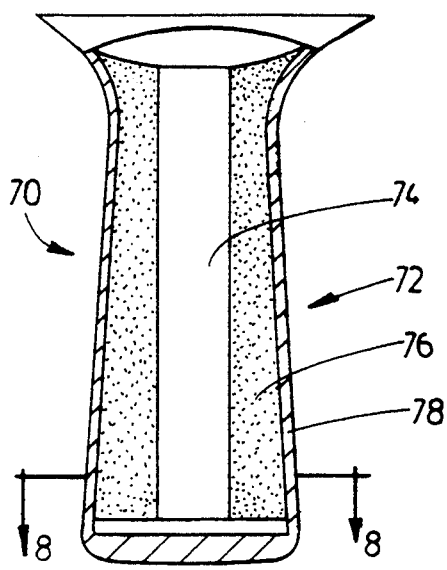
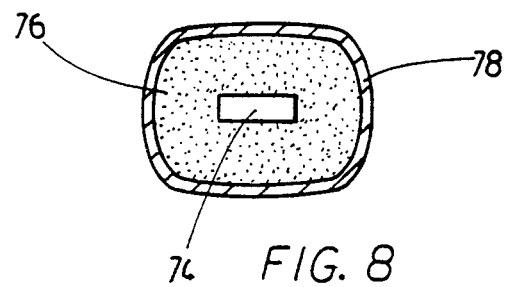
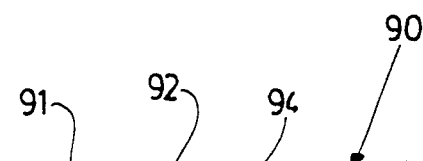
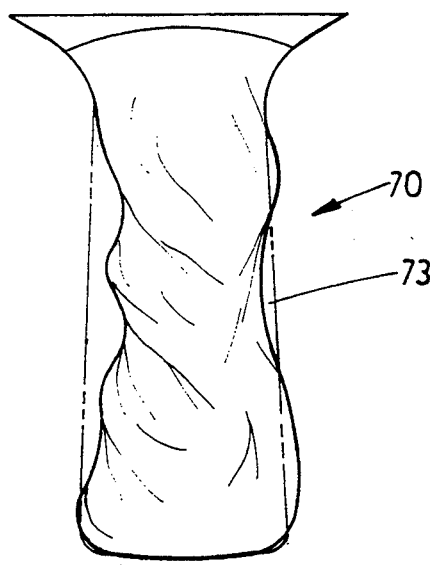
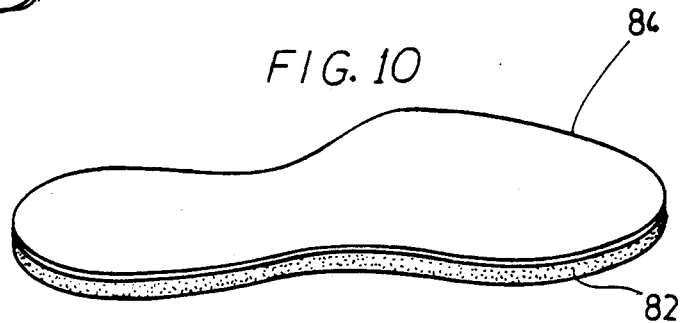

MOULDABLE COMPOSITION AND METHOD OF MAKING IT

This application is a continuation in part of U.S. patent application Ser. No. 07/992,752, filed Dec. 18, 1992 now abandoned, Title: Moldable Composition and Method of Making It, Inventor Robert Huybrechts.

FIELD OF THE INVENTION

The invention relates to a thermoplastic conformably re-moldable article and to a device incorporating such an article and in particular, to an orthopaedic support body repeatedly which is re-moldable to conform to portions of the body, and a method of forming a molded support article.

BACKGROUND OF THE INVENTION

Support devices, particularly orthopaedic supports are required in numerous circumstances. For example, supports may be required for any portions of the body, for disabled persons. Insoles may be required for shoes, to provide support for the feet. Joint supports may be required for various joints of the body which may have become injured or defective for any reason.

A support may be required for the head or neck, or back. A seat may be required conforming to the shape of an individual.

In addition, in very many cases supports are required for the hand or hands of a person suffering from some kind of disability, A person with no disability at all, may require to have a handle on an article which conforms precisely to the shape of his or her hand. Persons requiring such hand supports may simply require a shaped grip, which conforms precisely to the shape of their hand. Such persons may be craftsman, or it may be professionals such as surgeons, or may be sportsmen such as players of various games such as racquet sports, golf and the like or other sportsmen such as fishermen, hunters, and the like any of whom may require an article such as the handle of a golf club, fishing rod, or the stock of a weapon, to be shaped to particularly conform to the hand.

In most cases such a person will not be suffering from any disability, but will merely require a precise match between the shape of the hand grip and their hand. Conversely, persons suffering for example from arthritis of the fingers or other joints may require a hand grip of a peculiar shape, to conform to the somewhat deformed shape of their hand resulting from such a disability.

In the case of certain other sports, shoe, or boot liners may be required to conform precisely to the shape of the foot. This is particularly required for example in the sport of skiing where the boot is required to fit snugly under the instep and all over the foot.

Conformable support devices may also be required in many other cases other than orthopaedic situations. Such cases may arise in the case of packaging or containing of precision or scientific instruments, to prevent damage. Other cases may involve the provision of a shaped work support for holding a particular work piece, such as, an item of jewelry for example, while it is being worked upon.

In the past, various different systems have been proposed of more or less considerable complexity and expense. Orthopaedic supports requiring special forming and molding techniques are of course well known and are manufactured routinely from fast setting plaster materials. In other cases, supports have been shaped from bendable metal sections. In other cases, a complex multi-stage formation process is involved including the steps of making a "plug" in the shape of a limb, or portion of the body or an article, and them forming a support of glass fiber reinforced resin material, with or without padding. In other cases supports such as for example gun stocks are actually carved by hand out of wood, in an effort to as far as possible conform to the hand and body of the user.

Clearly, where such a conformable support device is required, it is desirable if it can be manufactured in a simple one step technique out of low cost materials. Preferably it will be made by direct contact with the portion of the body, or the article, which it is intended to support. In this way any loss of accuracy due to the making of intermediate articles such as plugs, molds and the like is avoided.

In the particular field of dentistry, it has been known to utilize settable materials for obtaining a form from the mouth or teeth. These settable materials are then used in a multi-stage process for making dentures, or denture supports, or for example making caps for teeth. Such settable materials are of such a nature that generally speaking they do not set completely hard, and are relatively easily distorted out of shape. Consequently, once the form has been taken from the mouth, the materials must then be treated with considerable care.

In the manufacture of dentures, it is customary for example that some parts of the denture shall be shaped so that support portions of the denture will actually fit on ridges formed by the gums, and thus be retained in position in the mouth.

It is however well known that in these cases the retention formations on the dentures must be made with great care. If they conform precisely to the shape of the ridges and grooves in the gums, then the insertion and removal of the dentures may cause considerable discomfort. On the other hand, if there is any substantial degree of clearance or play, then they may easily become displaced. The use of denture retention materials only partially overcomes this problem.

Clearly, it would be desirable if it were possible to incorporate in such a denture or denture plate, a moldable and settable portion, such that it could be inserted into the mouth, and then shaped to precisely fit the ridges and grooves in the gums, or fit the tongue to provide a secure retention of the denture plate within the mouth, and also to the floor of the mouth and to the bottom of the tongue, and furthermore that it could readily and easily be softened and reshaped and remolded from time to time or even on a daily basis, as the dentures are inserted and removed, or as often as is required, so as to ensure complete comfort for the wearer at all times.

Similarly, it is clearly desirable to provide a moldable body support for any other part of the body such as in the case of spectacles, which may be required to fit the bridge of the nose, or over the ear, which may readily be molded directly to conform to the shape of the body and will then retain its shape, for as long as is required, but which may be remolded and reshaped from time to time in accordance with the needs of the user.

Helmets may also advantageously be provided with liners conforming to the shape of the skull.

It is clearly desirable to provide such a moldable support for other purposes other than supporting parts of the body whether for orthopaedic purposes or otherwise, and which again will retain its shape, and which may yet be remolded readily from time to time.

The present invention addresses the above problems.

BRIEF SUMMARY OF THE INVENTION

With a view to solving the various problems and conflicting objectives described above, the invention comprises moldable settable article forming part of a personally portable device, the article being adapted for contact with the person, and being capable of repeated reheating and re-molding for repeated customization to the shape of the portion of the person by the user, the article comprising a thermoplastic composition which is set at ambient temperatures up to about 37° C., and which is conformably moldable at elevated temperatures in the region of between about 50° C. and 95° C. Preferably the thermoplastic composition comprises at least one acrylate polymer, for example, a methacrylate polymer. The methacrylate polymer may include polymer units of the formula:

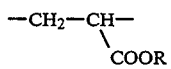

where R is an alkyl group having 1 to 4 carbon atoms. The methacrylate polymer may be mixed with a further methacrylate polymer, which may be polymethyl methacrylate polyethyl methacrylate or polybutyl methacrylate.

The thermoplastic composition plasticizer in an amount of from substantially 20-40% by weight of the methacrylate polymer.

The first methacrylate polymer and the further methacrylate polymer are present in a ratio of 1:1 to 1:2.5 by weight respectively.

The invention also includes a method of making a thermoplastic composition for use to form a moldable, settable article capable of customization to shape by a user, comprising mixing a liquid mixture of methacrylate monomer with plasticizer, mixing the liquid mixture with powdered solid methacrylate polymer and polymerization initiator, and polymerizing the methacrylate monomer at elevated temperature to form a composite whereby the resulting composition is set hard at temperatures up to about 37° C. and is conformably moldable at temperatures between about 50° C. and 95° C.

The plasticizer may be mixed with the acrylate monomer in an amount of from 20-40% by weight.

The liquid mixture is mixed with the powdered solid methacrylate polymer in ratio of from 1:1 to 1:2.5 by weight respectively.

The solid powdered methacrylate polymer should be at least substantially set at temperatures under 95° C. and the polymerization may be carried out to produce a polymer having which is substantially liquid at temperatures between 50° C. and 95° C. the polymerization initiator may be benzoyl peroxide.

The plasticizer may be dibutyl phthalate or dioctyl phthalate and mixtures thereof or other suitable plasticizer.

The invention also includes a moldable settable dental fixture comprising a base having an approximate generally desired shape and a body portion capable of customization to shape by a user, the body portion comprising a thermoplastic composition which is set at temperatures up to about 37° C. and conformably moldable at temperatures in the region of between about 50° C. and 95° C., and being capable of being reheated and re-molded repeatedly, even on a daily basis if necessary, to ensure both comfort and fit at all times.

The invention also includes a moldable, settable hand piece of an article to be held in the hand comprising a base having an approximate generally desired shape and a cover portion for said base, said cover portion comprising a thermoplastic composition which is set at temperatures up to 37° C. and conformably moldable at temperatures in the region of between 50° C. and 95° C.

The invention also includes a hand piece in which a layer of resilient, deformable, flexible material is interposed between the base and the cover portion.

The various features of novelty which characterize the invention are pointed out with more particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention.

BRIEF DESCRIPTION OF THE DRAWINGS

FIG. 7 illustrates the handle of an article, in this case a bat for playing table tennis, showing a conformable and moldable body in accordance with the invention thereon;

FIG. 8 shows a section of the handle, along line 8—8 of FIG. 7 surrounded by a resilient flexible material, completely wrapped into a layer of thermoplastic material;

FIG. 9 illustrates the handle of the article of FIG. 7, after being heated and molded to fit the form of a hand;

FIG. 10 shows an insole for a shoe according to the invention; and

FIG. 11 shows a protective helmet according to the invention, partially in section.

DETAILED DESCRIPTION OF A PREFERRED EMBODIMENTS

Figure 1:
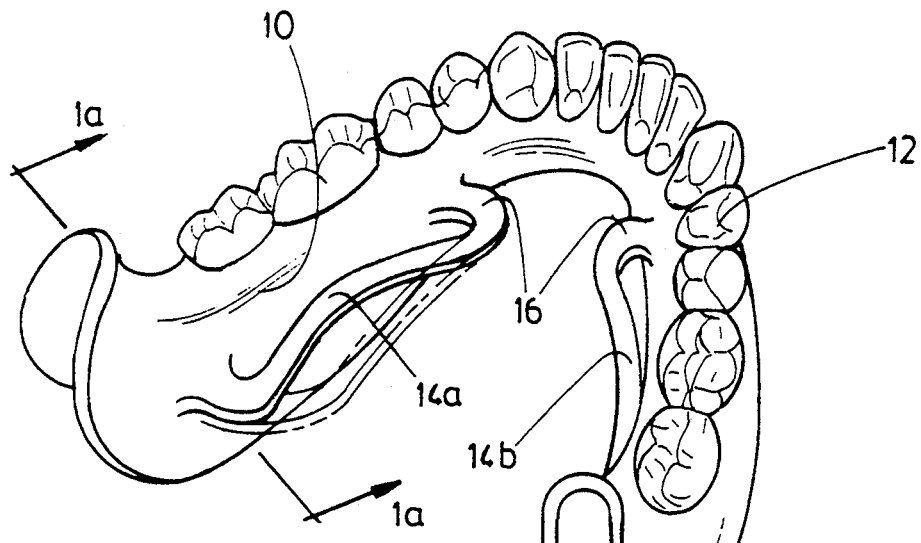
FIG. 1 is a perspective illustration of a typical lower denture, showing the moldable and conformable sublingual support devices formed of a material according to the invention attached to the inner walls of the denture.
Figure 1A:
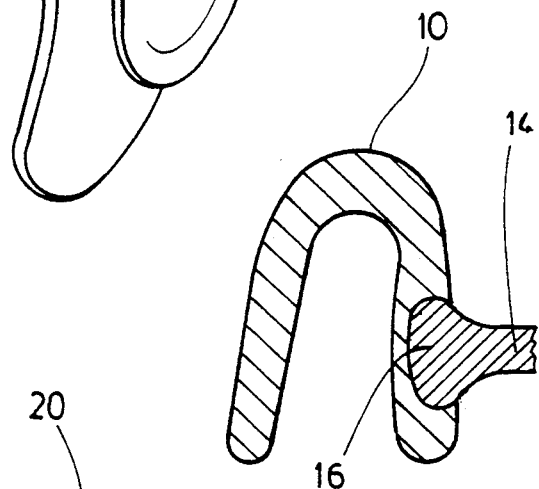
FIG. 1a is a section along line 1a–1a of FIG. 1.

As explained above, while the invention is of wide application to many fields, it is explained here principally in the field of its orthopaedic use, and in particular, in the field of dentistry. As is well known, the fitting of dentures and denture plates is a tiresome task both for the dentist and the patient. Molds are taken by the dentist, in order for him to as far as possible build a denture or denture plate which is shaped to conform to the mouth. Retention devices are often incorporated in dentures and denture plates to retain them in position. In some cases wire loops or hooks are incorporated in denture plates to engage either the teeth, or to lie under the tongue.

The fitting and bending and setting of these retention devices requires great care and skill. During actual use, the dentures are taken out at night and replaced in the morning, and must be fully cleansed. It is not unusual for dentures to become damaged, and in particular for the wire retention devices to become deformed. This then means that the denture must be returned to the dentist for refitting.

Even when fitted with great care, it is well known that denture plates often cause discomfort and become loose.

Denture retention materials, which are essentially formed of adhesive or mastic materials are well known, but are distasteful to use and are often only partially effective and are only deemed to be a temporary measure.

Clearly therefore the provision of retention devices on a denture plate which are essentially self fitting, so that the actual wearer can shape them and fit them to suit the wearer, and can repeat the fitting and molding operations as many times as is required. This will offer numerous advantages, and will substantially reduce the end cost of the dentures to the wearer.

In accordance with the invention as illustrated in FIGS. 1 to 6, a denture supports of different types are illustrated, each having a plurality of teeth secured thereto. Such denture supports, also known as denture plates, are made in a variety of shapes, depending upon the number of false teeth that it is desired to support within a person's mouth, and their location. Typical denture plates have the generally U shaped configuration as shown, to conform to the gums of the upper or lower jaw. In other cases, full denture plates, extending across the mouth from side to side are provided, where greatest support is required.

As is well known, the fitting of such denture supports to the gums and flesh of the interior of the mouth requires considerable time and skill. As mentioned above, such a fitting operation can never make a perfect fit to any individual. This is because a variety of reasons, including the difficulty of taking an accurate mold of the shape of a persons gums, the changes which take place in the shape of a persons gums from time to time, but most of all, from the fact that if an absolutely perfect fit is achieved, then inserting and removing the denture support may be extremely difficult if not impossible.

Accordingly, it is customary for wearers of dentures to retain the denture support in the mouth with some form of mastic or adhesive-like material. This is messy and distasteful, and is also known to be somewhat ineffective in many cases.

FIG. 1 shows a lower denture 10 formed of conventional material but having teeth 12 and two moldable conformable sublingual wings 14A, 14B. The sublingual wings are located to lie beneath the tongue of a wearer, and are illustrated as each having a U-shape, the legs of the U being short and the web being long in comparison to the legs. Such sublingual wings may be secured by means of a suitable permanent adhesive, or by thermoplastic material, or by thermosetting material. Whatever the material used, the ends of the legs 14a–14b define abutments 16 of the material, embedded in holes, grooves or slots in the denture.

The conformable sublingual wings 14A, 14B are formed of a material according to the invention of a type to be described below. The material is such that at normal ambient and body temperatures it is substantially hard and rigid. At somewhat elevated temperatures over 50° C., and usually between 50° C. and 95° C. the material becomes soft and moldable.

If the user wishes to adjust the molding of the sublingual devices 14A, and 14B, he may dip them in a cup of hot water to soften the material.

The dentures may then be placed in the mouth while the sublingual devices are still soft, and the molding may be adjusted by manipulating the sublingual devices with the fingers and/or with the tongue and/or the muscle on the bottom of the mouth. The sublingual devices can be molded to conform precisely to the interior shape of the mouth as suggested in phantom in FIG. 1. This process can be repeated as many times as necessary. That is to say the conformable parts or articles can be reheated, rendering them moldable, and after cooling they will again set hard.

Figure 2:
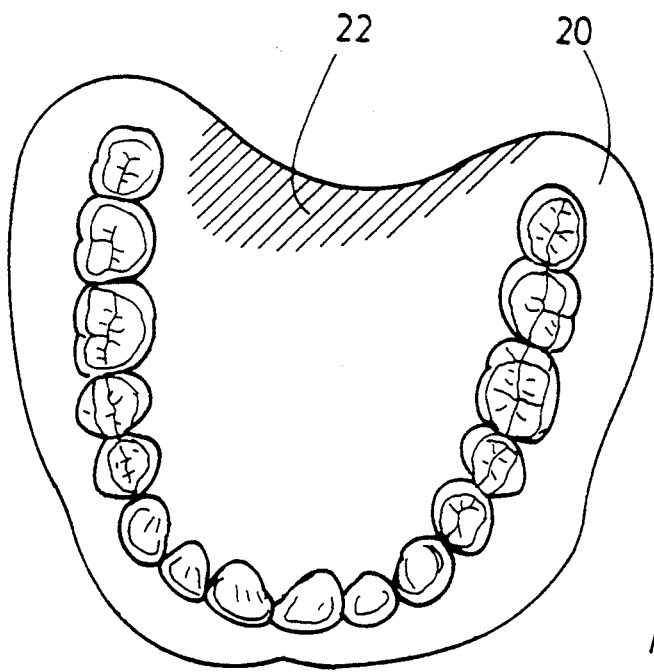
FIG. 2 is a top view of an upper denture plate and shows the area where a thermoplastic postdam formed of a material according to the invention would serve to seal the back edge of the plate, from air entering underneath the plate.

FIG. 2 illustrates an upper denture support 20 having teeth 22 and a postdam 24. Conventionally a postdam is constructed by scoring the stone model constructed from the impression molds, at the palatal periphery, by hand with a sharp instrument or by drill, more or less guessing at the depth and length of the postdam. The present invention allows the provision of a postdam region which is fully customizable to the patient's requirements.

Simply by immersing the denture in warm water for a minute, the dentist can now adjust the postdam in any way required. At body temperature the material will regain rigidity. The postdam can even be shortened if required, simply by cutting the material while still warm, with sharp scissors.

Figure 3:
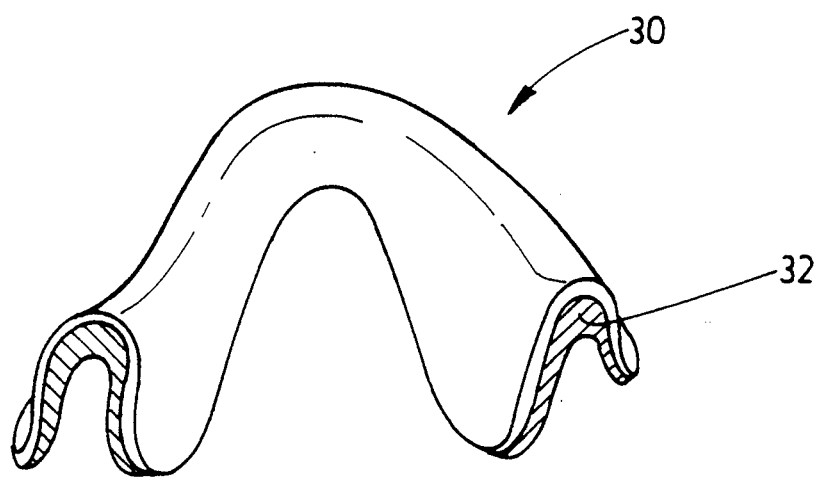
FIG. 3 shows a denture base made of a uniform thin layer of thermosetting acrylic plastics material and a layer of soft thermoplastic reline material according to the invention inside the denture.

FIG. 3 illustrates a denture 30 having a lining 32 of a material according to the invention. Such lining may be warmed in warm water and then conformed with the ridges and shape of the patients lower jaw. An upper denture may have a similar lining.

In the construction of conventional lower dentures, when the lower ridges are badly shrunk, often it is not possible to give the patient a stable prosthesis. Up to now the large undercuts, always existing near the back of the lingual aspect of the mandible, could not be utilized to stabilize the lower denture.

Figure 4:
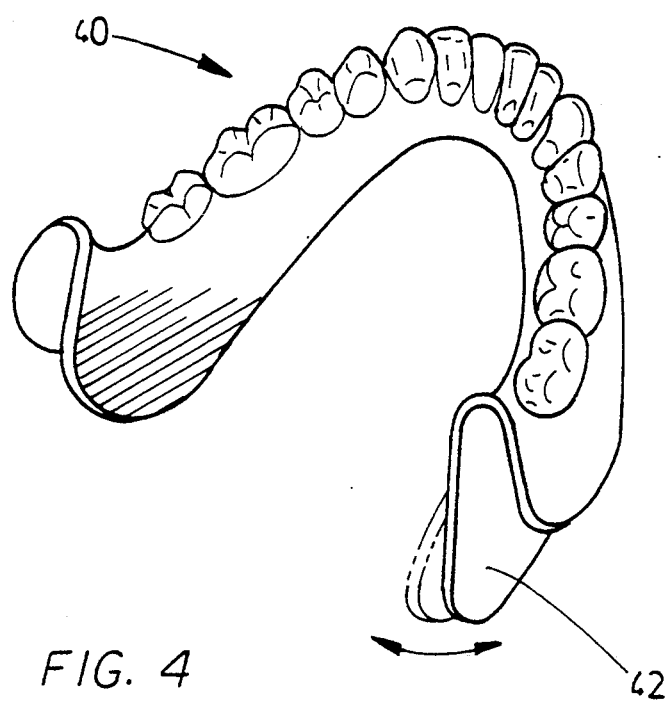
FIGS. 4 shows how the thermoplastic denture wall formed of a material according to the invention on a lower denture can be made to conform into the undercuts at the back of the lower gums.

The "undercuts" are, however, particularly suitable for receiving the moldable lingual aspects of a lower denture (FIG. 4). When the dentures 40 (or at least the rear lingual aspects 42 of a lower denture) is formed of material according to the invention. The moldable lingual aspects may be molded into these undercuts, to hook into them. A different position of one the lingual aspects 42 is shown in phantom lines. Thus the moldable lingual aspects may be bent in either direction of arrow A to hook into the undercuts or to disengage from them. The mouth may be rinsed with cold water to accelerate cooling and setting. Lingual aspects 42 may then remain substantially hard and rigid and retain the denture in position as long as the wearer wishes it to remain.

In order to remove the denture, all that the wearer has to do is to rinse the mouth with hot water. The heat will tend to soften the lingual aspects 42. This will then permit the wearer of the denture to simply grasp the denture with a finger and thumb and withdraw it from the mouth.

Figure 5:
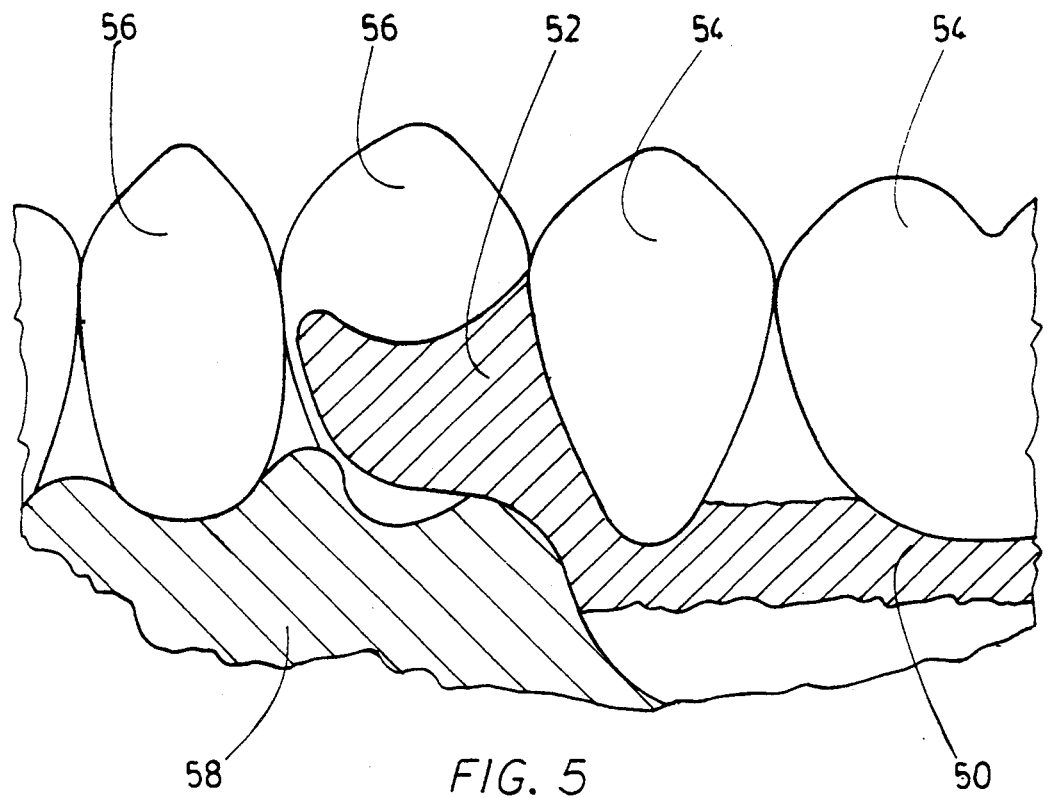
FIG. 5 shows an example of a partial denture, attaching artificial teeth to natural teeth, by means of a thermoplastic clasp formed of a material according to the invention.

In accordance with the formulations of the invention described below, this operation maybe carried out if desired on a daily basis repeatedly, each time the dentures are removed and reinserted. FIG. 5 illustrates part of a denture 50 including a clasp 52 for attaching artificial teeth 54 of the denture 50 to natural teeth 56 in the patient's gum 58. The clasp 52 is made of material according to the invention and may be attached in position very easily. The dentures with the clasp material is immersed in warm water and inserted into the mouth while still warm. The clasp 52 is molded firmly around the tooth 56 to which it is to be joined. A mouthful of cold water accelerates setting.

Figure 6:
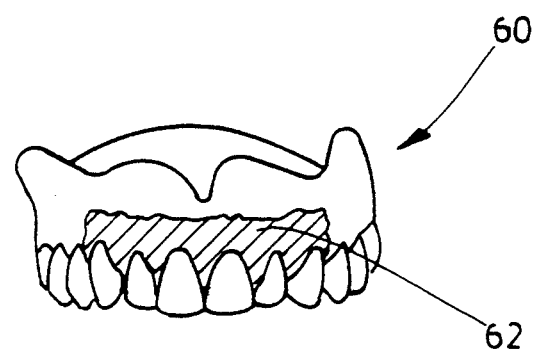
FIG. 6 shows six front teeth of a denture fixed into a layer of thermoplastic material according to the invention, to be moveable and adjustable when heated.

FIG. 6 illustrates the use of thermoplastic material according to the invention in the front aspect 62 of an upper denture 60. Again a firm bond, customized to the patient's mouth is easily achievable.

FIGS. 7, 8, and 9 illustrate the use of material according to the invention for a non-dental application, i.e. for custom molding the hand grip of a piece of sports equipment. Numerous such applications, such as helmets and other protective sportswear, splints, seating, shoe inserts and other foot wear, packing material, and the like, are also possible.

It will be appreciated that the general principal may be applied to any or all of these items as will be readily understood from the following description which is specific to the molding of a table tennis bat handle.

A table tennis bat 70 has a handle 72. The handle 72 comprises a central longitudinal core 74 optionally covered by a layer of compressible flexible material 76 such as foamed material. Over the layer of foamed material 76 or, if such material is not present, directly over the core 74 is an outer layer 78 of material according to the invention. The bat handle 72, before customization, may be roughly contoured to the shape of a hand gripping it or it may be substantially non-contoured. To customize the handle it is dipped in warm water and gripped by the user. The warm water softens the outer layer 78 to make it conformably moldable. The grip of the user, thereafter, molds the layer 78 as shown i.e. by molded handle 73 in FIG. 9 to his particular grip. Setting may be hastened by dipping the molded handle in cold water. The molding process may be repeated several times until the best grip is achieved. Alternatively the molding process may be repeated as the bat is used by different persons.

When warm water is referred to herein, it is meant that the temperature of the water is sufficient to make the material according to the invention become conformably moldable. This temperature is usually from 50° C. to 95° C.

From the possible range of uses of the material it will be appreciated that the set hardness will not necessarily be the same for all end uses. For example, a postdam region of a dental plate will generally be harder than a mouth guard or a table tennis bat handle.

FIG. 10 shows an insole for a shoe having a lower layer 82 formed of conventional insole material such as foam rubber. The insole also includes an upper layer 84 formed of the moldable, conformable composition of the invention. When the insole is heated to a temperature between about 50° C. and 95° C. the upper layer 84 becomes moldable. At a temperature within this range comfortable to the user the upper layer may be molded to fit the shape of the foot. Thereafter, at body temperature, the shape is retained. The process may be repeated several times i.e. the article may be reheated and remolded several times, to ensure the best possible fit. Alternatively it may be desirable to move the insoles from one pair of shoes to another, and again the articles can be reheated and remolded as required.

FIG. 11 shows a protective helmet 90 for example a hockey helmet, in general outline. A section of the helmet is cut away to show the outer shell 91, and foam padding 92. An upper portion of padding 92 is provided with an inwardly directed layer 94 of thermoplastic material according to the invention which is conformably moldable between 50° C. and 95° C. Such a hockey helmet may have the layer 96 molded to conform to the head contours of a user by heating the helmet to a temperature within the range of about 50° C. to 95° C. At a temperature comfortable to the user but within this range, the layer may be molded to the shape of the user's head. Thereafter, at body temperature the layer will retain its molded shape.

Various materials according to the invention and their method of preparation will now be described by way of example.

Examples 1-6

Conformably moldable compositions capable of repeated remolding were prepared as follows:

A monomer mixture was prepared according to the ingredients and proportions set out in Table I. A polymer powder mixture was prepared comprising 99 parts by weight of solid polyethylmethacrylate and one part by weight benzoyl peroxide which is a polymerization initiator.

TABLE I

| MONOMER LIQUID | MIX 1 | MIX 2 | MIX 3 | MIX 4 | MIX 5 | MIX 6 |
|---|---|---|---|---|---|---|
| 1. Methyl methacrylate (inhibited with hydroquinone 50 ppm) | 54.5 | 27.8 | 76.75 | 63.4 | 58.95 | 72.3 |
| 2. Butyl methacrylate | 5 | 8 | 2.5 | 4 | 4.5 | 3 |
| 3. Dibutyl phthalate | 22 | 35.2 | 11 | 17.6 | 19.8 | 13.2 |
| 4. Dioctyl phthalate | 18 | 28.8 | 9 | 14.4 | 16.2 | 10.8 |
| 5. Ethylene glycol dimethacrylate | 0.5 | 0.2 | 0.75 | 0.6 | 0.55 | 0.7 |

The compositions of liquid mixtures 1-6 were each mixed with the polymer powder mixture in a ratio of one part liquid mixture to two parts polymer powder mixture. Each of the resulting liquid monomer/solid polymers was held at 100° C. in boiling water for a period of 30 minutes to polymerize monomer, to result in six thermoplastic polymer compositions A-F. Each polymer composition was used to mold various articles at between 50° C. to 95° C. and each was found to be especially appropriate for the uses as set out in Table II.

TABLE II

| Thermoplastic material | Mixture used | Ratio by weight of liquid mixture: polymer powder | Use |
|---|---|---|---|
| A | 1 | 1:2 | Mouthguards TMJ Appliances. |
| B | 2 | 1:2 | Gasket clasps. |
| C | 3 | 1:2 | Postdam regions of dental plates, hand grips, sports equipment, splints |
| D | 4 | 1:2 | Dental clasps |
| E | 5 | 1:2 | Sublingual wings |
| F | 6 | 1:2 | Rear lingual aspect of lower dental plate |

It will be appreciated that the hardness or softness of the resulting product is dependent upon the proportion of methacrylate monomer used in the liquid monomer mixture B. It is possible to vary the ratio of liquid monomer to polymer powder within a range of, for example, 1:1 to 1:3 by weight.

Methyl methacrylate in the monomer liquid may be replaced by or mixed with any or all of ethyl-1, propyl or butyl methacrylate, or possibly even higher alkyl liquid methacrylates.

The polymerized ethyl methacrylate may be replaced by or mixed with solid polymethylmethacrylate, polypropylmethacrylate or polybutylmethacrylate. Other polymerization inhibitors are, of course possible but should only be present in an amount to inhibit premature polymerization prior to mixing with polymer. Many other variations and modifications are possible within the scope of the invention.

The foregoing is a description of a preferred embodiment of the invention which is given here by way of example only. The invention is not to be taken as limited to any of the specific features as described, but comprehends all such variations thereof as come within the scope of the appended claims.

What is claimed is:

1. A re-moldable settable dental article forming part of a dental fixture, said article being located on the exterior of said fixture for contact with the person and being capable of daily repeated reheating and remolding for repeated daily customization to the shape of a portion of the person by a user, and comprising, a thermoplastic polymerized composition which is set hard in air at ambient temperatures up to about 37° C. and which may be repeatedly rendered conformably moldable at elevated temperatures of between about 50° C. and 95° C. to be repeatedly re-molded during daily use to conform to the person, and which remains hard when in contact with the person and cooled to body temperature, said thermoplastic polymerized composition in turn consisting of;
   a liquid mixture of,
   a first predetermined quantity of liquid methyl methacrylate monomer in an amount of about 27 to 76 parts per hundred of said liquid mixture;
   a second predetermined quantity of liquid butyl methacrylate monomer in an amount of about 2.5 to 8 parts per hundred of said liquid mixture, and,
   a third predetermined quantity of a plasticizer mixture, in an amount of about 20 to 63 parts per hundred of said liquid mixture; and,
   a powdered polyethyl methacrylate polymer together with a polymerization initiator, mixed with said liquid mixture in a ratio of about from one part to about two parts by weight of powdered polyethyl methacrylate polymer, to about one part by weight of said liquid mixture, said powdered polyethyl methacrylate polymer being at least substantially set at temperatures below about 95° C., said liquid mixture and said powdered polyethyl methacrylate polymer in said composition being polymerized, whereby said polymerized composition remains set after polymerization at temperatures in the region up to about 37° C. and which may be repeatedly rendered substantially manually re-moldable in daily use at temperatures between about 50° C. and 95° C.

2. A re-moldable, settable dental article as claimed in claim 1, a thermoplastic polymerized composition as aforesaid wherein said plasticizer mixture comprises a mixture of dibutyl phthalate and dioctyl phthalate.

3. A re-moldable, settable dental article as claimed in claim 1 in which said liquid monomer mixture and said powdered polyethyl methacrylate polymer are present in a ratio of about 1:1.5 by weight respectively.

4. A re-moldable, settable dental article as claimed in claim 1 in which said liquid mixture includes ethylene glycol dimethacrylate as a cross-linking agent.

* * * * *